United States Patent
Martínez Piñeiro et al.

(10) Patent No.: US 11,653,866 B2
(45) Date of Patent: May 23, 2023

(54) PREDICTION OF THE OUTCOME OF ENDOVASCULAR TREATMENT IN ACUTE ISCHEMIC STROKE PATIENTS

(71) Applicant: FUNDACIÓ INSTITUT D'INVESTIGACIÓ EN CIÈNCIES DE LA SALUT GERMANS TRIAS I PUJOL, Badalona (ES)

(72) Inventors: Alicia Martínez Piñeiro, Barcelona (ES); Jaume Coll Cantí, Barcelona (ES)

(73) Assignee: FUNDACIÓ INSTITUT D'INVESTIGACIÓ EN CIÈNCIES DE LA SALUT GERMANS TRIAS I PUJOL, Badalona (ES)

( * ) Notice: Subject to any disclaimer, the term of this patent is extended or adjusted under 35 U.S.C. 154(b) by 775 days.

(21) Appl. No.: 16/605,189

(22) PCT Filed: Feb. 16, 2018

(86) PCT No.: PCT/EP2018/053899
§ 371 (c)(1),
(2) Date: Oct. 14, 2019

(87) PCT Pub. No.: WO2018/149973
PCT Pub. Date: Aug. 23, 2018

(65) Prior Publication Data
US 2020/0113462 A1   Apr. 16, 2020

(30) Foreign Application Priority Data
Feb. 17, 2017   (EP) ..................... 17382078

(51) Int. Cl.
*A61B 5/24*   (2021.01)
*A61B 5/02*   (2006.01)
(Continued)

(52) U.S. Cl.
CPC ............ *A61B 5/24* (2021.01); *A61B 5/02007* (2013.01); *A61B 5/029* (2013.01); *A61B 5/4005* (2013.01); *A61B 5/4842* (2013.01)

(58) Field of Classification Search
None
See application file for complete search history.

(56) References Cited

PUBLICATIONS

Shiban, Ehab, et al. "Predictive value of transcranial evoked potentials during mechanical endovascular therapy for acute ischaemic stroke: a feasibility study." Journal of Neurology, Neurosurgery & Psychiatry 87.6 (2016): 598-603. (Year: 2016).*

(Continued)

*Primary Examiner* — Jacqueline Cheng
*Assistant Examiner* — Jairo H Portillo
(74) *Attorney, Agent, or Firm* — Seed IP Law Group LLP

(57) ABSTRACT

The present application provides for use of a somatosensory evoked potential (SEP) during the hyperacute stroke phase as marker for predicting the outcome of endovascular treatment in a patient suffering from acute ischemic stroke, wherein when the SEP ipsilateral to the stroke site has an amplitude from 60% to 100% with respect to the corresponding SEP contralateral to the stroke site this is indicative of good outcome of the endovascular treatment, whereas when the SEP ipsilateral to the stroke site has an amplitude from 0% to 20% with respect to the corresponding SEP contralateral to the stroke site this is indicative of bad outcome of the endovascular treatment.

14 Claims, 1 Drawing Sheet

(51) Int. Cl.
*A61B 5/029* (2006.01)
*A61B 5/00* (2006.01)

(56) References Cited

PUBLICATIONS

Roosink et al. "Altered cortical somatosensory processing in chronic stroke: a relationship with post-stroke shoulder pain." NeuroRehabilitation 28.4 (2011): 67-92 (Year: 2011).*
Lee et al. "Prediction of good functional recovery after stroke based on combined motor and somatosensory evoked potential findings." Journal of Rehabilitation Medicine 42.1 (2010): 16-20 (Year: 2010).*
Scalzo, Fabien, May Nour, and David S. Liebeskind. "Data science of stroke imaging and enlightenment of the penumbra." Frontiers in neurology 6 (2015): 8. (Year: 2015).*
Vinciguerra, Luisa, and Julian Bosel. "Noninvasive neuromonitoring: current utility in subarachnoid hemorrhage, traumatic brain injury, and stroke." Neurocritical Care 27.1 (2017): 122-140. (Year: 2017).*
Malcharek, M. J., et al. "Intraoperative monitoring of carotid endarterectomy by transcranial motor evoked potential: a multicenter study of 600 patients." Clinical Neurophysiology 124.5 (2013): 1025-1030. (Year: 2013).*
U.S. Appl. No. 16/757,263, filed Apr. 17, 2020.
U.S. Appl. No. 16/760,179, filed Apr. 29, 2020.
Barber et al., "Validity and reliability of a quantitative computed tomography score in predicting outcome of hyperacute stroke before thrombolytic therapy," *Lancet 355*:1670-1674, 2000.
Goldstein et al., "Interrater Reliability of the NIH Stroke Scale," *Arch. Neurol. 46*:660-662, 1989.
Haupt et al., "Contribution of initial median-nerve somatosensory evoked potentials and brainstem auditory evoked potentials to prediction of clinical outcome in cerebrovascular critical care patients: a statistical evaluation,"*Journal of Clinical Neurophysiology 15*(2):154-158 , 1998.
Higashida et al., "Trial Design and Reporting Standards for Intra-Arterial Cerebral Thrombolysis for Acute Ischemic Stroke," *Stroke 34*:e109-e137, 2003. (31 pages).
Moazffarian et al., "Heart Disease and Stroke Statistics—2015 Update: A Report From the American Heart Association," *Circulation 131*:e29-e322, 2015, (297 pages).
Nuwer et al., "IFCN recommended standards for short latency somatosensory evoked potentials. Report of an IFCN committee," *Electroencephalography and clinical Neurophysiology 91*:6-11, 1994.
Pfaff et al., "Mechanical Thrombectomy in Patients with Acute Ischemic Stroke and Lower NIHSS Scores: Recanalization Rates, Periprocedural Complications, and Clinical Outcome," *AJNR Am J Neruoradiol 37*:2066-2071, 2016.
Saver, "Novel End Point Analytic Techniques and Interpreting Shifts Across the Entire Range of Outcome Scales in Acute Stroke Trials," *Stroke 38*:3055-3062, 2007.
Zhang et al., "Somatosensory and Brainstem Auditory Evoked Potentials Assessed between 4 and 7 Days after Severe Stroke Onset Predict Unfavorable Outcome," *BioMed Research International 2015*:196148, 6 pages, 2015.

* cited by examiner

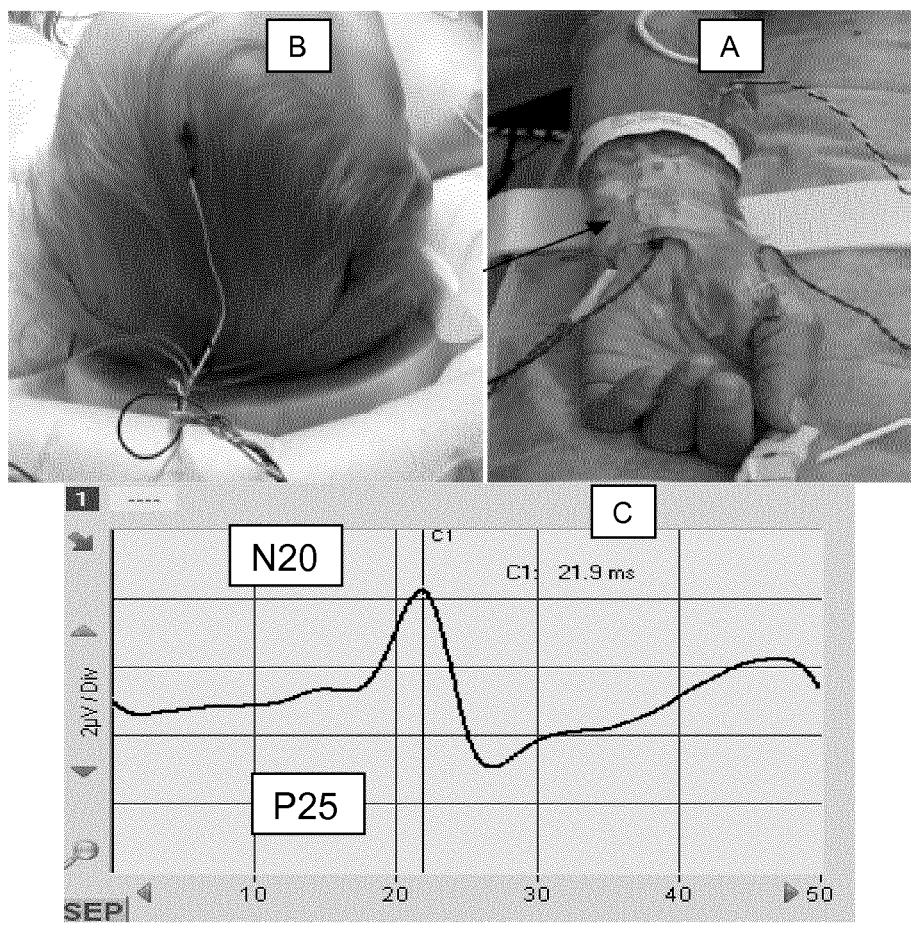

PREDICTION OF THE OUTCOME OF ENDOVASCULAR TREATMENT IN ACUTE ISCHEMIC STROKE PATIENTS

This application claims the benefit of European Patent Application EP17382078.8 filed Feb. 17, 2017.

TECHNICAL FIELD

The present invention is related to the field of medicine, and particularly to the field of brain stroke. The invention provides means to predict the outcome of endovascular treatment in patients suffering from an acute ischemic stroke.

BACKGROUND ART

A brain stroke is a cerebral circulation disorder which causes a transient or definitive alteration of the functioning of one or several parts of the brain. The affectation of specific areas of the brain by brain strokes generates focalized manifestations such as paralysis of one half of the body (hemiplegia), facial paralysis, aphasia (loss of the capacity to produce or understand language) and disorientation, among others. In general, the symptoms of strokes are variable depending on the brain area affected. In milder cases, the consequences may go unnoticed and may not be greatly limiting for the patient due to the anodyne nature of the symptoms. However, strokes frequently cause permanent neuronal damage or result in the death of the individual. Indeed, brain stroke is one of the main causes of mortality and of permanent incapacity in adults in the majority of developed countries (Executive Summary: Heart Disease and Stroke Statistics-2015 Update. A report from the American Heart Association. Circulation 2015 Jan. 27, 131(4): e29-322).

According to its aetiology, the brain stroke may be ischemic or haemorrhagic. An ischemic stroke arises when the brain loses blood supply due to the sudden and immediate interruption of blood flow, which frequently occurs due to the occlusion of any of the arteries that supply the brain matter because of a blood clot. In contrast, the haemorrhagic stroke is triggered by the rupture of an encephalic blood vessel due to a hypertensive peak, a congenital aneurism, or other less frequent causes. Acute ischemic stroke is caused by thrombotic or embolic occlusion of a cerebral artery The management of acute ischemic stroke is a major healthcare challenge. Over the last 15 years, advances in acute ischemic stroke management have led to a significant reduction in the morbidity and mortality related to this serious disease. Once the diagnosis of acute ischemic stroke is confirmed by imaging techniques upon arrival of the patient at the hospital, the etiological work up is conducted in parallel with therapeutic measures by stroke units.

Intravenous administration of recombinant tissue plasminogen activator (tPA) has been widely used in emergency stroke management. Although intravenous tPA improves survival and functional outcomes when administered as early as possible after onset of ischemic stroke, its use is limited by the narrow therapeutic time window (nowadays the therapeutic window is <4.5 hours, although this time might be extended to <6 hours, depending on the results of ongoing clinical trials) and by important contraindications, including coagulopathy, recent surgery, or stroke or head injury within the past 3 months, among others. Ultimately, only a limited percentage of patients presenting with ischemic stroke can be eligible for treatment with intravenous tPA.

The limitations of intravenous tPA have led to interest in endovascular therapy for acute ischemic stroke, in particular, intraarterial thrombolysis and mechanical thrombectomy. Compared with intravenous tPA, endovascular treatment can recanalize large arterial occlusions earlier and more frequently. Whether this translates into more favorable clinical outcomes was assessed in randomized clinical trials that evaluated outcomes of endovascular therapy vs intravenous tPA for ischemic stroke. From 2015, several landmark trials have established the safety and efficacy of endovascular treatment against best medical treatment in patient with large vessel occlusion of the anterior cerebral circulation. According to the positive results of these trials, the endovascular approach for acute ischemic stroke treatment has been included in the paradigm of stroke therapeutics and, nowadays, it is part of stroke centers daily routine.

The selection of patients that can benefit from endovascular intervention is usually made according to several clinical variables and neuroimaging parameters. Among the clinical variables, special attention is given to age, baseline NIHSS score (National Institute of Health Stroke Scale), systolic blood pressure and hyperglycemia. Regarding neuroimaging parameters, computed tomography (CT) and magnetic resonance imaging (MRI) have proved useful to provide crucial information such as infarct core, ischemic penumbra/degree of collaterals, vessel occlusion, and thrombus that helps in the selection of the best candidates for endovascular treatment. Nonetheless, the achievement of a complete arterial recanalization by means of endovascular treatment does not always lead to optimal clinical and functional recovery. Despite major advances in stroke therapeutics and using predictive factors based on clinical and neuroimaging criteria for selecting patients candidates for the endovascular treatment, the likelihood of significant disability or death after three months from stroke onset remains between 40 and 67%.

This raises the question of whether the outcome of endovascular intervention can be prognosticated. Early knowledge on the outcome of the endovascular intervention would provide valuable information on the best therapeutic approach for the patient and to avoid innecesary risks.

In view of the above there is still a need to provide methods to improve stratification of patients candidates for endovascular treatment in order to determine a priori who of them could benefit and in whom it will be futile.

SUMMARY OF INVENTION

The inventors have surprisingly found that somatosensory evoked potentials (SEPs) may predict clinical outcome of endovascular therapy such as mechanical thrombectomy in patients suffering from acute ischemic stroke. Thus, monitoring of SEPs before the endovascular treatment of acute ischemic stroke is useful to identify early which patients are better candidates for endovascular treatment or, in other words, for which patients the endovascular treatment will be most effective.

In a first aspect the present invention provides for use of a somatosensory evoked potential (SEP) during the hyperacute stroke phase as marker for predicting the outcome of endovascular treatment in a patient suffering from acute ischemic stroke. When the SEP ipsilateral to the stroke site has an amplitude from 60% to 100% with respect to the corresponding SEP contralateral to the stroke site this is indicative of good outcome of the endovascular treatment, whereas when the SEP ipsilateral to the stroke site has an amplitude from 0% to 20% with respect to the corresponding SEP contralateral to the stroke site this is indicative of bad outcome of the endovascular treatment.

The invention also provides a method for predicting the outcome of endovascular treatment in a patient suffering from acute ischemic stroke, said method comprising:

(i) eliciting a SEP ipsilateral to the stroke site of the patient during the hyperacute stroke phase, and (ii) determining the presence of the SEP.

When the SEP ipsilateral to the stroke site has an amplitude from 60% to 100% with respect to the corresponding SEP contralateral to the stroke site this is indicative of good outcome of the endovascular treatment, whereas when the SEP ipsilateral to the stroke site has an amplitude from 0% to 20% with respect to the corresponding SEP contralateral to the stroke site this is indicative of bad outcome of the endovascular treatment.

SEPs recording is a non-invasive, feasible and economical test that can be made in any hospital to predict the outcome of a complex and highly invasive intervention such as thrombectomy.

The prognostic value of SEPs is effectively shown in the examples below. Those patients presenting a basal N20 response ipsilateral to the stroke site showed a better neurologic evolution in the first 24 h after the ictus, as well as 7 days after the ictus, most of them even showing a dramatic neurologic and functional recovery.

Altogether, SEPs provide early knowledge of predictive data that would speed up therapeutic decision making in patients suffering from acute ischemic stroke.

Therefore the invention also provides for use of a SEP for deciding or recommending to perform an endovascular treatment in a patient suffering from acute ischemic stroke. Patients showing a good prognosis according to SEP as defined above would better benefit from endovascular treatment, so that this medical intervention would be recommended.

The invention also provides a method of deciding or recommending to perform endovascular treatment in a patient suffering from acute ischemic stroke, which method comprises: (i) eliciting a SEP ipsilateral to the stroke site of the patient, and (ii) determining the presence of the SEP. Again, when a good outcome of endovascular treatment is predicted according to SEP as disclosed above, this medical intervention would be recommended.

Finally, in a third aspect the invention also discloses use of a SEP for stratifying acute isquemic stroke patients with regard to their likelihood to benefit from endovascular treatment.

The invention also discloses a method of stratifying acute isquemic stroke patients with regard to their likelihood to benefit from endovascular treatment, which method comprises the steps of (i) eliciting a SEP ipsilateral to the stroke site of the patient, and (ii) determining the presence of the SEP.

BRIEF DESCRIPTION OF DRAWINGS

FIG. 1 shows SEPs methodology. A. Stimulation at wrist (adhesive or bar surface electrodes). B. Transcraneal recording according to modified international 10-20 system. C. Median SEP defined by two major deflections: negative (N20) and positive (P25) waves

DETAILED DESCRIPTION OF THE INVENTION

Evoked potential (EP) tests measure the electrical activity of the brain that results after applying an stimulus from different types of sensory modalities (sight, sound, or touch). Somatosensory evoked potentials is a useful, noninvasive means of assessing somatosensory system functioning. SEP components include a series of positive and negative deflections that can be elicited by sensory stimuli. They are most commonly elicited by bipolar trancutaneous electrical stimulation applied on the skin over the trajectory of peripheral nerves of the upper limb (e.g., the median nerve) or lower limb (e.g., the posterior tibial nerve), and then recorded from the scalp.

Median nerve SEP begins with the delivery of an electrical stimulus to median or ulnar nerve at the wrist. A 100-300 microsecond square wave electrical pulse is delivered at intensities strong enough to cause a 1-2 cm thumb twitch. Upon delivery of such a stimulus, nerve action volleys travel up sensory fibers and motor fibers to the shoulder, producing a peak as they enter. This peak is formally known as N9. In the course of conduction, the sensory fibers then transverse the cervical roots and enter the cervical cord. The median nerve pathway then joins the posterior columns, sending off collateral branches to synapse in the midcervical cord. This midcervical cord activity gives rise to a peak known as N13. The N13 is best measured over the fifth cervical spine. Further conduction in the posterior columns passes through the synapse at the cervicomedullary junction and enters the lemniscal decussation. A scalp P14 peak is generated at this level. As conduction continues up the medial lemniscus to upper midbrain and into the thalamus, a scalp negative peak is detected, the N18. After synapsing in the thalamus and traversing the internal capsule, the N20 is recorded over the somatosensory cortex contralateral to the wrist stimulated, corresponding to arrival of the nerve impulses at the primary somatosensory region.

Thus, for eliciting a SEP, a nerve has to be stimulated. A SEP response is then obtained. In particular embodiments the SEP is obtained by stimulating the median nerve or, alternatively, the ulnar nerve. For obtaining a response ipsilateral to the stroke site, a nerve, such as the median nerve or ulnar nerve, contralateral to the stroke site needs to be stimulated. In practical terms both median nerves or both ulnar nerves are stimulated, for example, by means of surface adhesive electrodes. Generaly the nerves are stimulated at the wrist. A target SEP response is then obtained in both ipsilateral and contralateral sides to the stroke site. The SEP contralateral to the stroke site (the "healthy" side) is used as control, whereas the corresponding SEP ipsilateral to the stroke site (the "impaired" side) provides the prognostic information. As illustrative information, FIG. 1 shows SEPs methodology.

According to the present invention, when the SEP ipsilateral to the stroke site is present this is indicative of good prognosis, whereas when the SEP ipsilateral to the stroke site is absent this is indicative of bad prognosis. The amplitude of the target SEP may also be determined providing for a more comprehensive prognostic value. In particular, when the SEP ipsilateral to the stroke site has an amplitude from 60% to 100% with respect to the corresponding SEP contralateral to the stroke site this is indicative of good prognosis, whereas when the SEP ipsilateral to the stroke site has an amplitude from 0% to 30% with respect to the corresponding SEP contralateral the stroke site this is indicative of bad prognosis.

"Good prognosis" is herein understood as the likelyhood of a good outcome of the endovascular treatment. A good outcome is understood as a modified Rankin scale 0-2 at 90 days (after the endovascular therapy). More specifcally, a good outcome with dramatic recovery is understood as an improvement ≥10 or NIHSS score 0-1 at 24 hours, as well as modified Rankin scale 0-2 at 90 days. NIHSS is the National Institutes of Healt Stroke Scale, a systematic assessment tool that provides a quantitative measure of stroke-related neurologic deficit. The Rankin scale is a commonly used scale for measuring the degree of disability or dependence in the daily activities of people who have suffered a stroke or other causes of neurological disability. It has become the most widely used clinical outcome measure for stroke clinical trials. "Bad prognosis" is defined as a modified Rankin scale >3 at 3 months after the stroke onset. The terms "prognosis" and "prediction" are used interchangebly in the present application.

The invention also provides a method for the prognosis of the outcome of endovascular treatment in a patient suffering from acute ischemic stroke, said method comprising:

(i) eliciting a SEP ipsilateral and contralateral to the stroke site of the patient, (ii) Determining the SEP ipsilateral and contralateral to the stroke site, wherein when the SEP ipsilateral to the stroke site has an amplitude from 60% to 100% with respect to the corresponding SEP contralateral to the stroke site this is indicative of good prognosis, whereas when the SEP response ipsilateral to the stroke site has an amplitude from 0% to 30% with respect to the corresponding SEP contralateral to the stroke site this is indicative of bad prognosis.

More particularly, when the SEP ipsilateral to the stroke site has an amplitude from 75% to 100% with respect to the corresponding SEP contralateral to the stroke site this is indicative of good prognosis, whereas when the SEP response ipsilateral to the stroke site has an amplitude from 0% to 20% with respect to the corresponding SEP contralateral to the stroke site this is indicative of bad prognosis. More particularly, when the SEP ipsilateral to the stroke site has an amplitude from 80% to 100% with respect to the corresponding SEP contralateral to the stroke site this is indicative of good prognosis, whereas when the SEP response ipsilateral to the stroke site has an amplitude from 0% to 15% with respect to the corresponding SEP contralateral to the stroke site this is indicative of bad prognosis. More particularly, when the SEP ipsilateral to the stroke site has an amplitude from 85% to 100% with respect to the corresponding SEP contralateral to the stroke site this is indicative of good prognosis, whereas when the SEP response ipsilateral to the stroke site has an amplitude from 0% to 10% with respect to the corresponding SEP contralateral to the stroke site this is indicative of bad prognosis.

Measurement of the SEP is state of the art for the skilled person (Nuwer, M R, Aminoff, M, Demedt, J, Eisen, A A, Goodin, D, Matsuoika, S, Mauguiere, F, Shibasaki H, Sutherling, W and Vibert, J F (1994) IFCN recommended standars for short latency somatosensory evoked potentials: report of an IFCN committee. Electroencephalogra. Clin. Neuorphysiol., 91: 6-11). Such measurements are practical routine for the hospital staff with application in a wide variety of clinical applications, such as diagnosis in patients with neurologic diseases, to evaluate patients with sensory symptoms that might be psychogenic, for prognostication in comatose patients, and for intraoperative monitoring during surgeries that place parts of the somatosensory pathways at risk.

In particular embodiments, the SEP is determined by stimulating the median nerve or, alternatively, the ulnar nerve. The SEP is then selected from the N20 and P25 components. In one particular embodiment of the invention the SEP is the N20 component. The N20 is a negativity that typically peaks at 20 milliseconds after the stimulus. It is recorded over the somatosensory cortex contralateral to the wrist stimulated, corresponding to arrival of the nerve impulses at the primary somatosensory region. To obtain a prognostic information, the median nerve or the ulnar nerve contralateral to the stroke site is stimulated and the N20 or P25 ipsilateral to the stroke site is measured. In another embodiment the SEP is the P25 component. P25 is recognized as the main prominent positive peak succeeding the N20 wave.

In particular embodiments, the SEP is determined by stimulating the tibial nerve. The SEP is then selected from the N35 or P40 components. In one particular embodiment of the invention the SEP is the N35 component. In another embodiment the SEP is the P40 component. To obtain a prognostic information, the tibial nerve contralateral to the stroke site is stimulated and the N35 or P40 ipsilateral to the stroke site is measured. P40 is the major positive peak located in the post-central scalp region. It may be preceded by a slight negative potential, the N35 component.

SEPs can then be used as a neurophysiological markers providing prognostic information on the outcome of endovascular therapy in acute ischemic stroke patients when said SEPs are measured before the surgical intervention. Since the therapeutic window for endovascular treatment is very narrow (usually the intervention should be performed within 8 hours from stroke onset), the SEPs as prognostic markers must be determined as soon as the patient enters the hospital. This means the SEP is determined during the hyperacute stroke phase. "Hyperacute stroke phase" refers to the phase where key interventions involved in the assessment, stabilization and treatment in the first hours after stroke onset. This will represent all pre-hospital and initial emergency care for ischemic stroke. This includes thrombolysis or endovascular interventions for acute ischemic stroke, emergency neurosurgical procedures, and risk stratification evaluation. The principal aim of this phase of care is to diagnose the stroke type, and to coordinate and execute the treatment plan as rapidly as possible. Broadly speaking "hyperacute" refers to the first 24 hours after stroke. In preferred embodiments the "hyperacute stroke phase" refers to patients presenting within 8 hours, preferably within 6 hours, of stroke onset. In particular embodiments, the SEP is determined within 8 h from stroke onset, preferably within 6 h from stroke onset. This timing can be established if the time of stroke onset can be determined, even if approximately. Often, however, the time of stroke onset cannot be determined. In such cases, the SEP is determined within 120 min from the arrival of the patient at the hospital, preferably within 90 min from the arrival of the patient at the hospital. A time "within" X min or h from stroke onset means that monitoring of SEPs may take place seconds after the stroke onset until X min or h after stroke onset. Similarly, a time "within" X min or h from min from the arrival of the patient at the hospital means that monitoring of SEPs may take place the moment the patient arrives at the hospital until X min or h after arrival. Usually this could also be expressed as from 1 s to X min or h after stroke onset or after arrival at the hospital.

Patients that may better benefit from using SEPs as prognostic marker of good outcome of endovascular therapy are those for which these type of therapy is indicated. In particular embodiments, the patient suffering from acute ischemic stroke presents with anterior large vessel occlusion, with or without stenosis or internal ipsilateral carotid occlusion. In some embodiments, the patient presents with anterior large vessel occlusion with stenosis or ipsilateral internal carotid occlusion. In some embodiments, the patient presents with anterior large vessel occlusion without stenosis or ipsilateral carotid artery occlusion. In some embodiments, the patient presents with proximal middle cerebral artery occlusion. In another particular embodiment the patient presents a clinical status as defined by NIHSS equal or above 10.

SEPs also provide useful information when determined during the endovascular intervention and shortly after the intervention is finished. During the intervention, SEPs monitoring provides real time data about de functional brain status, guiding the neuroradiologist strategy and optimizing the hemodynamic conditions of the patient depending on the data obtained.

Data provided by SEPs monitoring could act individually as prognostic marker or in combination with the already known predictive factors such as baseline NIHSS score, computed tomography and magnetic resonance imaging data. Further, SEPs also provide good prognostic information when patients are under anesthesia or induced coma, when a clinical neurological asesment can not be performed.

As mentioned above, the invention also provides methods for deciding or recommending to perform endovascular treatment in a patient suffering from acute isquemic stroke and for stratifying acute isquemic stroke patients with regard to their likelyhood to benefit from endovascular treatment.

In one embodiment, the method for deciding or recommending to perform endovascular treatment in a patient suffering from acute isquemic stroke comprises:
(i) eliciting a SEP ipsilateral to the stroke site of the patient,
(ii) determining the presence of the SEP, and
(iii) recommending to perform endovascular treatment if the SEP is present.

In another embodiment, the method for deciding or recommending to perform endovascular treatment in a patient suffering from acute isquemic stroke comprises:
(i) eliciting a SEP ipsilateral and contralateral to the stroke site of the patient,
(ii) determining the SEP ipsilateral and contralateral to the stroke site, and
(iii) recommending to perform endovascular treatment if the SEP ipsilateral to the stroke site has an amplitude from 60% to 100% with respect to the corresponding SEP contralateral to the stroke site (i.e. if a good prognosis is found).

In a further embodiment, the method for deciding or recommending to perform endovascular treatment in a patient suffering from acute isquemic stroke comprises:
(i) stimulating both median nerves or, alternatively, both ulnar nerves of the patient, preferably at the wrist,
(ii) determining the SEP ipsilateral and contralateral to the stroke site, and
(iii) recommending to perform endovascular treatment if the SEP ipsilateral to the stroke site has an amplitude from 60% to 100% with respect to the corresponding SEP contralateral to the stroke site (i.e. if a good prognosis is found).

In another embodiment, the method for stratifying acute isquemic stroke patients with regard to their likelyhood to benefit from endovascular treatment comprises:
(i) eliciting a SEP ipsilateral to the stroke site of the patient,
(ii) determining the presence of the SEP, and
(iii) stratifying the patient as being likely to benefit from endovascular treatment if the SEP is present.

In another embodiment, the method for stratifying acute isquemic stroke patients with regard to their likelyhood to benefit from endovascular treatment comprises:
(i) eliciting a SEP ipsilateral and contralateral to the stroke site of the patient,
(ii) determining the SEP ipsilateral and contralateral to the stroke site, and
(iii) stratifying the patient as being likely to benefit from endovascular treatment if the SEP ipsilateral to the stroke site has an amplitude from 60% to 100% with respect to the corresponding SEP contralateral to the stroke site (i.e. if a good prognosis is found).

In another embodiment, the method for stratifying acute isquemic stroke patients with regard to their likelyhood to benefit from endovascular treatment comprises:
(i) stimulating both median nerves or, alternatively, both ulnar nerves, of the patient, preferably at the wrist,
(ii) determining the SEP ipsilateral and contralateral to the stroke site, and
(iii) stratifying the patient as being likely to benefit from endovascular treatment if the SEP ipsilateral to the stroke site has an amplitude from 60% to 100% with respect to the corresponding SEP contralateral to the stroke site (i.e. if a good prognosis is found).

Recommending to perform endovascular treatment or stratifying the patient as being likely to benefit from endovascular treatment is preferably done if the SEP ipsilateral to the stroke site has an amplitude from 75% to 100%, or from 80 to 100%, with respect to the corresponding SEP contralateral to the stroke site. The SEP to be determined is selected from N20 and P25, preferably N20. Aternatively, instead of the median or ulnar nerves, the tibial nerve may be stimulated. The SEP to be determined is then selected from N35 and P40. The SEP is preferably determined in the hyperacute ischemic stroke phase, more preferably within 6 h from stroke onset in those patients for which stroke onset can be determined or, alternatively, within 90 min from the arrival of the patient to the hospital. The patient suffering acute ischemic stroke preferably presents with anterior large vessel occlusion, with or without stenosis or internal ipsilateral carotid occlusion. In particular embodiments, the patient presents with proximal middle cerebral artery occlusion.

"Endovascular therapy" is understood as the (early) recanalization of occluded vessels in acute ischemic stroke (AIS) either by intraarterial thrombolysis or endovascular thrombectomy. These proceedures have been shown to be associated with improved clinical outcome and reduced mortality in recent major clinical trials. Intra-arterial thrombolysis is an emerging treatment strategy where the cervicocephalic arterial tree is traversed with an endovascular microcatheter delivery system. The catheter port is positioned immediately within and adjacent to the offending thrombus, and fibrinolytic agents are infused directly into the clot. This delivery technique permits high concentrations of lytic agent to be applied to the clot while minimizing systemic exposure.

Mechanical thrombectomy is understood as the delivery of a retrieval device to a thromboembolus that is occluding a cerebral artery to directly remove the thrombus. Mechanical thrombectomy devices can remove a clot in a matter of minutes, whereas pharmaceutical thrombolytics, even those delivered intra-arterially, may take as long as 2 hours to dissolve a thrombus. The most recently developed devices, known as retrievable stents or stentrievers, have shown higher recanalization rates and better outcomes than those seen with the older Merci Retriever.

In particular embodiments of the present invention the endovascular treatment preferably comprises mechanical thrombectomy. In other embodiments, the endovascular treatment comprises intra-arterial thrombolysis. In some embodiments, the endovascular treatment comprises mechanical thrombectomy and intra-arterial thrombolysis. In other embodiments, the endovascular treatment, preferably mechanical thrombectomy, is performed in combination with intravenous administration of tPA.

Throughout the description and claims the word "comprise" and variations of the word, are not intended to exclude other technical features, additives, components, or steps. Furthermore, the word "comprise" encompasses the case of "consisting of". The following examples and drawings are provided by way of illustration, and they are not intended to be limiting of the present invention.

EXAMPLES

1. Methodology

Patients.

Patients were included with acute ischemic stroke and anterior large vessel occlusion (proximal middle cerebral artery occlusion), with or without ipsilateral internal carotid artery (ICA) significant stenosis or occlusion, underwent endovascular treatment. The patients were diagnosed by computed tomography angiography (CTA) or magnetic resonance imaging (MRI). Exclusion criteria included well documented story of neuromuscular disorders, stroke or central nervous system tumors that could interfere in the SEPs assessment.

Clinical Data.

Clinical and anthropometrical variables were registered: age, sex, location of intracranial occlusion, type of treatment and the presence of cardiovascular risk factors as arterial hypertension, Diabetes Mellitus, dyslipidemia and obesity. The severity of stroke was evaluated by means of National Institutes of Healt Stroke Scale (NIHSS) score (Goldstein L B, Bartels C, Davis J N (1989) Interrater reliability of the NIH Stroke Scale. Arch Neurol. 46 660-662) at the moment of the admission, after the endovascular treatment, at 24 hours, one week or at the moment of being discharged and 3 months after the onset of symptoms. The variable "dramatic neurological recovery", defined as an improvement higher than 10 points in the NIHSS at the first 24 hours or a NIHSS score of 0-1 at first 24 hours, was assessed. Functional outcome was assessed by modified Rankin Scale (mRS) (Saber J L. Novel end point analytic techniques and interpreting shifts across the entire range of outcome scales in acute stroke trials. Stroke 2007; 38:3055-62) at one week or at the moment of being discharged and 3 months after the onset of symptoms. Good functional outcome was defined as a mRS score equal to or greater than 2 at 3 months after the onset of symptoms. Medical and neurological complications during hospital admission were also recorded.

Neuroimaging.

Basal neuroimaging was performed, indistinctly, by: non-contrast head computed tomography (NCCT), perfusion computed tomography (CTP) or multiparametric MRI. A multimodal neuroimagen previously to the endovascular treatment was sometimes obtained. All images were analyzed jointly by a neuroradiologist and neurologist. They were blinded to the clinical data apart from the side of acute symptoms.

Computed tomography (CT). The Alberta Stroke Program Early Computed Tomographic Score (ASPECTS) (Barber P A, Demchuk A M, Zhang A M; ASPECTS Study Group. Alberta Stroke Programme Early CT Score. Validity and reliability of a quantitative computed tomography score in predicting outcome of hyperacute stroke before thrombolytic therapy. Lancet. 2000; 355:1670-1674) was assessed from admission NCCT. Hemorrhagic transformation was evaluated from control NCCT. The site of occlusion as well as collateral circulation was assessed by means of CTA. Perfusion CT allowed to evaluate perfusion maps of cerebral blood flow (CBF), cerebral blodd volume (CBV), mean transit time (MTT) and time-to-maximum (TMax) parameter. A significant mismatch was defined as CBV-MTT>20%.

Magnetic resonance imaging (MRI). All studies were performed on a 3.0T (Siemens Numaris/4 version SyngoB17, with a craneal coil of 32 channels) MR system. Imaging protocol included the following sequences: 1) survey, 2) Axial brain study with sequences: a) SWI/EPI-gradient recalled echo (GRE), b) Difussion weighted imaging (Dwi), c) fluid attenuation inversion recovery imaging (FLAIR), d) Angio-MRI time of flight (TOF) which includes Willis polygon, f) Angio-MRI 4D (dynamic postcontrast angiography) and g) Perfusion study, which was performed immediately after dynamic study. All images were anonymised and stored in DICOM format. Reviewers performed a visual analysis of qualitative variables and a quantitative analysis (tissue volume and intensity or signal units) of post-processed variables: first-pass permeability and perfusion maps. The post-process and analysis of Dwi, perfusion and permeability maps sequences were done using Olea Sphere platform. The remaining variables were analyzed with the Osirix 64 program.

The following variables were evaluated:

Volume and site of ischemic lesion (baseline and control MRI)

Area that shows restriction of water diffusion with an apparent diffusion coefficient ADC value less than 600

Volume and degree of hyperintensity of brain parenchyma impaired in fluid attenuation inversion recovery imaging (FLAIR) sequence Site of occlusion (baseline and control MRI): site of occlusion in TOF and dynamic angio-MR sequences and presence of blooming artifact in GRE sequence.

Collateral circulation status (baseline and control MRI): Willis polygon assessment by TOF sequence. Quantity and quality of collateral circulation in dynamic angio-MRI after defining a leptomeningeal collaterality score based on angiographic scales.

T2 first-pass of contrast brain perfusion (DSC: dynamic susceptibility contrast): volume of tissue impaired in rCBV, rCBF, MTT and TMax maps and volume of tissue with a delay in TMax>2 sec, TMax>4 sec, TMax>6 sec and TMax>8 sec. Tissue at ischemis risk was defined as having that volume with a delay in TMax>6 sec.

Hemorrhagic transformation (control MRI)

Angiography Variables.

The site of occlusion and the degree of arterial recanalization were assessed according to modified Thrombolysis in cerebral infarction (TICI) criteria that define a complete recanalization as TICI 2b and 3 (Higashida R T, Furlan A J, Roberts H et al. Trial design and reporting standards for intra-arterial cerebral thrombolysis for acute ischemic stroke. Stroke 2003; 34 (8): e109-137). Other clinical variables recorded were the moment of the groin puncture and arterial recanalization, blood pressure (baseline and periodically during the procedure).

Neurophysiological Monitoring.

Evoked potentials recordings were performed by 10 channels electromyographic system Medelec Synergy (Vyasys Healthcare) and the intraoperative monitoring system OSIRIS (Inomed Medizintechnik GmbH).

Somatosensory Evoked Potentials (SEPs).

Both median nerves were stimulated at wrist by means of surface adhesive electrodes. Supramaximal stimulation was defined as the intensity that causes visually perceptible movement of the stimulated limb. Square wave electrical pulses of 0.2-0.5 ms duration were applied at a frequency of 5.7 or 6.7 Hz. SEPs were recorded in a referential fashion from the C3' (right median nerve stimulation) and C4' (left median nerve stimulation) positions and from a reference electrode at Fpz (international 10-20 system) or Cz' electrodes (2 cm behind Cz). Needle electrodes were used if patients are awake or "cork screw" electrodes if patients were under general anesthesia during the procedure. The signal was digitally filtered (5-200 Hz bandpass) and analyzed within 80 msec time window poststimulus. Twenty to one hundred fifty trials were averaged depending on the signal-to-noise ratio. The target signal was the presence of N20 response ipsilateral to the stroke site. Secondarily, the amplitude and latency of N20 response both ipsilateral and contralateral to the stroke site were also measured.

SEPs recordings were performed during the hyperacute phase (first 6 hours from the onset of the symptoms), before the endovascular treatment and continuously during the procedure. Because there could also be neurological damage during reperfusion, SEPs recordings were prolonged until the patient was transferred to the Acute Stroke Unit.

Statistical Considerations.

Statistics were performed with the SPSS 19.0 statistical package. Chi squared test was used for comparisions of categorical variables, whereas t-Student, Mann-Whitney and Kruskal-Wallis were used for continuous variables.

2. Results

This was a prospective study. 42 patients were included. Six were excluded because of traces artifacts and one due to the absence of follow up at 3 months after the onset of the stroke. Final sample size is 35 patients. Average age was 68.5 years old (11.5DE) and 65.7% were men. All patients scored between 0 and 2 in the modified Rankin Scale (mRS) at the moment of its inclusion (79.5% had a mRS score of 0) Nineteen patients (54.3%) presented with a stroke due to proximal occlusion (M1 of middle cerebral artery (MCA), 8 (22.9%) because of terminal internal carotid artery (TICA) occlusion, 6 (17.1%) because of TANDEM occlusion (ICA and MCA simultaneuously), 1 (2.9%) because of proximal internal carotid artery (ACI) proximal and 1 (2.9%) due to TANDEM occlusion (ICA and TICA simultaneously). Regarding to the type of treatment received, 18 patients (51.4%) underwent primary endovascular treatment and 17 (48.6%) endovascular treatment after intravenous thrombolysis.

2.1. Neurophysiological Variables

Feasible and reproducible SEPs recording was achieved in 36 patients, representing 85.7% (36/42) of the total sample size. Thus, in this study, SEPs reproducibility was 85.7%.

The target signal was the N20 response. The presence, amplitude and latency of N20 response both ipsilateral and contralateral to the stroke site were measured during two specific moments of the endovascular treatment: baseline and at the end of the procedure.

At the beginning of the procedure, patent SEP was observed in 25 patients and absence of SEP wave in 10 patients. Age, gender, median NIHSS score (17 vs 17), site of vessel occlusion, intravenous thrombolysis (IV tPA) use, ASPECTS score and onset-to-groin puncture time were comparable between patients with patent and absent SEPs. Patent SEP group showed better median NIHSS score at 24 hours (6 [2-18] vs 18 [11-24], p=0.031) and 7 days (2[13] vs 17[19], p=0.030) and a non significant trend to a higher rate of dramatic recovery and good functional outcome at 7 days (52% vs 25%, p=0.087) and good functional outcome (mRs2) at the moment of being discharged (11 vs 1, p=0.060) (Table 1). Medical complications during the first 3 days after the onset of the stroke and number of deaths during the first week after the onset of symptoms were also comparable between both groups.

TABLE 1

Primary and secondary outcomes evaluation in patients with presence or absence of SEPs response before starting the endovascular treatment (baseline) (N = 35) (univariate analysis)

|  | Baseline SEP present (n = 25) | Baseline SEP absent (n = 10) | p |
|---|---|---|---|
| Dramatic recovery-n(%) |  |  |  |
| Yes | 13 (52) | 2 (20) | 0.087 |
| No | 12 (48) | 8 (80) |  |
| mRS 90 d-n(%) |  |  |  |
| 0-2 | 13 (56.5) | 3 (33.3) | 0.217 |
| ≥3 | 10 (43.5) | 6 (66.7) |  |
| NIHSS 24 h |  |  |  |
| Median (IQA) | 6 (19) | 18.50 (21) | 0.030 |
| NIHSS 7 d |  |  |  |
| Median (IQA) | 2 (13) | 17 (19) | 0.030 |
| mRS 7 d-n(%) |  |  |  |
| 0-2 | 11 (44) | 1 (10) | 0.060 |
| ≥3 | 14 (56) | 9 (90) |  |

At the end of the procedure, patent SEP was found in 25 patients (3 recovered and 3 lost SEP response). Complete revascularization (TICI 2b,3) was achieved in 22/25 patent SEP group and 4/10 no patent SEP group. Again, there were no statistical significant differences regarding age, sex, baseline NIHSS, site of the occlusion, iv rTPA use, ASPECTS score and onset-to-groin puncture time between both groups. Patent SEP at the end of the procedure was significantly associated with dramatic recovery (60% vs 0%, p=0.001) and early and long term good functional outcome (Table 2).

TABLE 2

Primary and secondary outcomes evaluation in patients with presence or absence of SEPs response at the end of the endovascular treatment (final) (N = 35) (univariate analysis)

|  | Final N20 present (n = 25) | Final N20 absent (n = 10) | p |
|---|---|---|---|
| Dramatic recovery-n(%) |  |  |  |
| Yes | 15 (60) | 0 | 0.001 |
| No | 10 (40) | 10 (100) |  |

TABLE 2-continued

Primary and secondary outcomes evaluation in patients with presence or absence of SEPs response at the end of the endovascular treatment (final) (N = 35) (univariate analysis)

|  | Final N20 present (n = 25) | Final N20 absent (n = 10) | p |
|---|---|---|---|
| mRS 90 d-n(%) |  |  |  |
| 0-2 | 16 (69.6) | 0 | <0.001 |
| ≥3 | 7 (30.4) | 9 (100) |  |
| NIHSS 24 h |  |  |  |
| Median (IQA) | 5 (9) | 23.50 (13) | <0.001 |
| NIHSS 7 d |  |  |  |
| Median (IQA) | 2 (9) | 19.50 (19) | <0.001 |
| mRS 7 d-n(%) |  |  |  |
| 0-2 | 12 (48) | 0 (0) | 0.006 |
| ≥3 | 13 (52) | 10 (100) |  |

DISCUSSION

First result to highlight is that SEP reproducibility is very high (85.7%), even taking into account they were performed during the hyperacute phase of the stroke in patients awake and with spontaneous ventilation. This is a feasible, reproducible and non-invasive methodology which could be performed at the bedside of patients.

On the other side, according to the data from experimental SEPs models of arterial brain ischemia, we did not expect that the patients included in the study (all of them with a large vessel occlusion and with NIHSS score≥10) would present presence of ipsilateral SEPs to the stroke site with latencies and amplitudes almost symmetrical with the contralateral site (healthy brain hemisphere).

Patients with presence of SEPs at the beginning of the procedure had better clinical outcome, expressed by NIHSS at first 24 hours and 7 days after the stroke and a non-significant trend to a higher rate of dramatic recovery and good functional outcome at 7 days (p=0.06). This lack of total statistical significance could be due to the small sample size.

The previous results were even more compelling if SEPs response remained stable or reappeared during the endovascular procedure. Patients with patent SEPs at the end of the procedure had better early and long term clinical outcome (p=0.001). From all this, two remarkable facts emerge. Presence of baseline SEP could act as predictive factor of good clinical and functional outcome after the endovascular treatment. Furthermore, its continuous monitoring during the procedure would provide real time data about the cerebral cortex functional status, guiding the neuroradiologist strategy as well as optimizing patient's haemodynamic condition if there were a SEP tendency for decreasing.

Currently, clinical algorithms for the acute ischemic stroke due to large vessel occlusion are mainly based on clinical and neuroimaging predictive factors for the stratification of patients candidates for endovascular treatment. However, the likelihood of significant functional disability or death three months after the stroke still ranges from 40 until 67%. SEPs act as neurophysiological markers and provide additional and different data respect that provided by the rest of predictive factors (NIHSS, blood pressure, hyperglycemia, ASPECTS, ischemic penumbra, collateral circulation status). Therefore, they could be included in the diagnostic and therapeutic algorithms of the acute ischemic stroke due to large vessel occlusion for improving the indication of endovascular treatment.

CITATION LIST

Executive Summary: Heart Disease and Stroke Statistics-2015 Update. A report from the American Heart Association. Circulation 2015 Jan. 27, 131(4):e29-322.

Nuwer, M R, Aminoff, M, Demedt, J, Eisen, A A, Goodin, D, Matsuoika, S, Mauguiere, F, Shibasaki H, Sutherling, W and Vibert, J F (1994) IFCN recommended standars for short latency somatosensory evoked potentials: report of an IFCN committee. Electroencephalogra. Clin. Neuorphysiol., 91: 6-11.

Goldstein L B, Bartels C, Davis J N (1989) Interrater reliability of the NIH Stroke Scale. Arch Neurol. 46 660-662

Saber J L. Novel end point analytic techniques and interpreting shifts across the entire range of outcome scales in acute stroke trials. Stroke 2007; 38:3055-62.

Barber P A, Demchuk A M, Zhang A M; ASPECTS Study Group. Alberta Stroke Programme Early CT Score. Validity and reliability of a quantitative computed tomography score in predicting outcome of hyperacute stroke before thrombolytic therapy. Lancet. 2000; 355:1670-1674.

Higashida R T, Furlan A J, Roberts H et al. Trial design and reporting standards for intra-arterial cerebral thrombolysis for acute ischemic stroke. Stroke 2003; 34 (8): e109-137

CLAUSES

1. Use of a somatosensory evoked potential (SEP) ipsilateral to the stroke site for the prognosis of the outcome of endovascular treatment in a patient suffering from acute ischemic stroke.

2. The use according to claim 1, wherein when the SEP ipsilateral to the stroke site has an amplitude from 60% to 100% with respect to the corresponding SEP contralateral to the stroke site this is indicative of good prognosis, whereas when the SEP ipsilateral to the stroke site has an amplitude from 0% to 20% with respect to the corresponding SEP contralateral to the stroke site this is indicative of bad prognosis.

3. The use according to any of the claims 1-2, wherein the SEP is determined by stimulating the median nerve or, alternatively, the ulnar nerve.

4. The use according to claim 3, wherein the SEP is selected from the N20 and P25 components.

5. The use according to claim 4, wherein the SEP is N20.

6. The use according to any of the claims 1-2, wherein the SEP is determined by stimulating the tibial nerve.

7. The use according to claim 6, wherein the SEP is selected from the N35 and P40 components.

8. The use according to any of the claims 1-7, wherein the SEP is determined during the hyperacute stroke phase.

9. The use according to claim 8, wherein the SEP is determined within 8 h from stroke onset or, alternatively, within 120 min from the arrival of the patient at the hospital.

10. The use according to claim 9 wherein, the SEP is determined within 6 h from stroke onset or, alternatively, within 90 min from the arrival of the patient at the hospital.

11. The use according to any of the claims 1-10, wherein the patient presents with anterior large vessel occlusion.

12. The use according to any of the claims 1-11, wherein the patient presents a clinical status as defined by the National Institutes of Health Stroke Scale (NIHSS) equal or above 10.

13. Use of a SEP for deciding or recommending to perform endovascular treatment in a patient suffering from acute ischemic stroke.

14. Use of a SEP for stratifying acute isquemic stroke patients with regard to their likelyhood to benefit from endovascular treatment.

15. The use according to any of the claims 1-14, wherein the endovascular treatment is mechanical thrombectomy.

The invention claimed is:

1. A method for treating a patient suffering from acute ischemic stroke, the method comprising:
   determining a somatosensory evoked potential (SEP) during a hyperacute stroke phase before endovascular treatment of the patient, wherein an SEP ipsilateral to a stroke site having an amplitude from 60% to 100% with respect to a corresponding SEP contralateral to the stroke site reflects a desired response to endovascular treatment; and
   if the determined SEP reflects the desired response to the endovascular treatment, providing the endovascular treatment to the patient, wherein the endovascular treatment comprises intraarterial thrombolysis, mechanical thrombectomy, or a combination thereof.

2. The method according to claim 1, wherein the SEP is determined by stimulating a median nerve or, alternatively, an ulnar nerve.

3. The method according to claim 2, wherein the SEP is selected from the N20 and P25 components.

4. The method according to claim 3, wherein the SEP is N20.

5. The method according to claim 2, wherein the patient presents with anterior large vessel occlusion.

6. The method according to claim 2, wherein the patient presents a clinical status as defined by the National Institutes of Health Stroke Scale (NIHSS) equal or above 10.

7. The method according to claim 1, wherein the SEP is determined by stimulating the tibial nerve.

8. The method according to claim 7, wherein the SEP is selected from the N35 and P40 components.

9. The method according to claim 8, wherein the SEP is determined within 8 h from stroke onset or, alternatively, within 120 min from arrival of the patient at a hospital.

10. The method according to claim 9, wherein the SEP is determined within 6 h from stroke onset or, alternatively, within 90 min from the arrival of the patient at the hospital.

11. The method according to claim 7, wherein the patient presents with anterior large vessel occlusion.

12. The method according to claim 7, wherein the patient presents a clinical status as defined by the National Institutes of Health Stroke Scale (NIHSS) equal or above 10.

13. The method according to claim 1, wherein the patient presents with anterior large vessel occlusion.

14. The method according to claim 1, wherein the patient presents a clinical status as defined by the National Institutes of Health Stroke Scale (NIHSS) equal or above 10.

\* \* \* \* \*